United States Patent [19]

Jacobs

[11] Patent Number: 5,312,364
[45] Date of Patent: May 17, 1994

[54] INTRAOSSEOUS INFUSION DEVICE

[75] Inventor: Michael W. Jacobs, Surrey, Canada

[73] Assignee: Pyng, Delta, Canada

[21] Appl. No.: 103,428

[22] Filed: Aug. 6, 1993

[51] Int. Cl.$^5$ .............................................. A61M 5/32
[52] U.S. Cl. .................................... 604/180; 604/272; 604/174
[58] Field of Search ................ 604/174, 180, 264, 272, 604/279, 51, 188, 93

[56] References Cited

U.S. PATENT DOCUMENTS

| | | |
|---|---|---|
| 1,272,104 | 7/1918 | Riethmueller . |
| 1,523,068 | 1/1925 | Hein . |
| 2,426,535 | 8/1947 | Turkel . |
| 2,705,949 | 4/1955 | Silverman . |
| 2,773,500 | 12/1956 | Young . |
| 2,773,501 | 12/1956 | Young . |
| 3,310,051 | 3/1967 | Schulte . |
| 3,469,574 | 9/1969 | Durkan . |
| 3,750,667 | 8/1973 | Pshenichny et al. . |
| 3,783,876 | 1/1974 | Dye . |
| 3,896,810 | 7/1975 | Akiyama ........................ 604/272 |
| 4,170,993 | 10/1979 | Alvarez ......................... 604/180 |
| 4,373,810 | 4/1983 | Ishizaki et al. . |
| 4,496,342 | 1/1985 | Banko ............................ 604/27 |
| 4,534,756 | 8/1985 | Nelson ........................... 604/50 |
| 4,645,492 | 2/1987 | Weeks ........................... 604/174 |
| 4,710,171 | 12/1987 | Rosenberg ..................... 604/117 |
| 4,743,231 | 5/1988 | Kay et al. ...................... 604/180 |
| 4,747,414 | 5/1988 | Brossel .......................... 604/87 |
| 4,763,667 | 8/1988 | Manzo ........................... 604/164 |
| 4,772,261 | 9/1988 | Von Hoff et al. .............. 604/264 |
| 4,969,870 | 11/1990 | Kramer et al. ................. 604/51 |
| 5,137,518 | 8/1992 | Mersch .......................... 604/168 |
| 5,176,643 | 1/1993 | Kramer et al. ................. 604/135 |
| 5,176,662 | 1/1993 | Bartholomew et al. ........ 604/180 |

OTHER PUBLICATIONS

Tocantins, et al., "Infusions of Blood and Other Fluids Via the Bone Marrow in Traumatic Shock and Other Forms of Peripheral Circulatory Failure," Annals of Surgery, vol. 114, No. 6, Dec., 1941, pp. 1085-1092.

Turkel, et al., "A New and Simple Instrument for Administration of Fluids Through Bone Marrow," War Medicine 5: 1944, pp. 222-225.

Shoor, et al., "Intraosseous Infusion: Pressure-Flow Relationship and Pharmacokinetics," The Journal of Trauma, vol. 19, No. 10, Oct. 1979, pp. 772-774.

Rosetti, et al., "Intraosseous Infusion: An Alternative Route of Pediatric Intravascular Access," Annals of Emergency Medicine, Sep., 1985.

Spivey, et al., "Comparison of Intraosseous, Central, and Peripheral Routes of Sodium Bicarbonate Administration During CPR in Pigs," Annals of Emergency Medicine, Dec. 1985: 14:12 1135-1140.

Berg, "Emergency Infusion of Catecholamines Into Bone Marrow," AJDC, vol. 138, Sep. 1984, pp. 810-811.

Rogers, et al., "Intraosseous Infusions," Cli. Procedures in Emergency Medicine, 1985, pp. 339-343.

Hodge, et al., "Intraosseous Infusion Flow Rates in Hypovolemic Pediatric Dogs," Annals of Emergency Medicine, 16:3 Mar. 1987, pp. 305 ∝ 307.

Primary Examiner—John G. Weiss
Attorney, Agent, or Firm—Pretty, Schroeder, Brueggemann & Clark

[57] ABSTRACT

An intraosseous infusion device includes a base and an upper frame mounted to the base. An elongated needle is fixed to the upper frame. A fitting is provided for receiving liquid to be delivered to a patient's bone marrow and for supplying the liquid to a bore in the needle. The base includes a cam surface and the upper frame includes a cam follower. The cam surface is configured to cause the upper frame to rotate relative to the base as the needle moves longitudinally between a retracted position within the base and an extended position below the base.

11 Claims, 2 Drawing Sheets

INTRAOSSEOUS INFUSION DEVICE

BACKGROUND OF THE INVENTION

This invention relates generally to intraosseous infusion devices and, in particular, to such a device having a self-rotating needle that is insertable a predetermined depth into the bone of a patient.

Drugs and other liquids are customarily delivered to patients via their vascular systems, using a needle or catheter inserted into a peripheral blood vessel. Such techniques function generally satisfactorily in cases where the patient's blood pressure is at normal levels. However, in cases where the patient is in circulatory shock due to heart failure, drug overdose, or severe hemorrhaging, the peripheral blood vessels frequently are collapsed and access to those blood vessels can be difficult. Peripheral vessel catherization also is exceedingly difficult in pediatric patients because of the small size of their peripheral vessels. Substantial delays in administering the drugs and liquids can therefore result and, in many instances, vascular access cannot be obtained at all. Severe injury to the patient, even death, can therefore result.

In such cases of serious circulatory shock and hemorrhaging, one suitable alternative to vascular infusion is intraosseous infusion. In particular, the resuscitative fluid or drug solution is injected directly into the bone marrow of the patient's bone. Typically, the sternum, femur, tibia, or other long bone located near the skin is used. Intraosseous infusion also is sometimes used on newborns and small children when suitable blood vessels cannot easily be accessed. Intraosseous infusion requires the penetration by a needle or the like of the patient's skin and outer bone to gain access to the bone marrow.

One device used for intraosseous infusion includes an infusion tube or needle having an enlarged threaded tip that is threaded into the bone. See, e.g., U.S. Pat. No. 4,969,870 to Kramer et al. With this device, the bone marrow is known to be reached when continued rotation of the threaded tip no longer advances the needle into the bone. This is because the bone marrow typically has insufficient structural integrity to be threaded. Once the threaded tip is placed in the bone marrow, liquid can be infused through a port located in the threaded tip. This device, however, has a drawback in that it requires an operator to continuously monitor the resistance to penetration during threading. Additionally, the enlarged tip often damages the outer bone and also leaves a hole in the outer bone for possible leakage of infused liquid.

Other intraosseous infusion devices are known that insert the needle a fixed depth into the patient's bone. Typically, a collar or other stop is fixed on the needle's shaft to indicate when the needle has penetrated the patient's body a sufficient depth that is estimated to be within the bone marrow. Such devices, however, often require complicated mechanisms to drive the needle into the bone, see e.g., U.S. Pat. No. 5,176,643 to Kramer et al. Other devices utilize a drill to thread the needle into place or require a significant amount of operator manipulation during insertion of the needle. See, e.g., U.S. Pat. Nos. 1,523,068, 2,773,500 and 2,773,501.

It should, therefore, be appreciated that there is a need for an improved intraosseous infusion device that provides assured access to the bone marrow without requiring significant operator manipulation or monitoring. Such a device would also permit infusion of drugs, plasma, etc. into the bone marrow with little damage to the bone itself or leakage of the infused liquid. The present invention satisfies this need.

SUMMARY OF THE INVENTION

The present invention is embodied in a simple, easy to use, intraosseous infusion device that is self-threading and that provides assured access to the bone marrow of a patient. The device includes an elongated needle that results in little damage to the bone during insertion and little leakage from the bone of liquids infused into the bone marrow.

The intraosseous infusion device of the present invention includes a base having a lower surface configured for placement against the skin of the patient. An upper frame is mounted to the base and the elongated needle is fixed to the upper frame. A fitting is provided for receiving liquid to be delivered to the patient's bone marrow and for supplying the liquid to a bore in the needle. In the preferred embodiment, the base includes a cam surface and the upper frame includes a cam follower. The cam surface is configured to cause the upper frame to rotate relative to the base as the needle moves longitudinally between a retracted position within the base and an extended position below the base. Rotation of the needle assists in bone penetration and eliminates or substantially reduces bone splintering caused by direct (non-rotating) piercing. Rotation of the needle during access also eliminates or substantially reduces the possibility of blockage of the needle ports due to the "coring" effect present in non-pencil point type needles.

The longitudinal distance travelled by the needle between the retracted and extended positions is fixed by the length of the cam surfaces in the longitudinal direction. Alternatively, the base may include a positive stop that contacts the upper frame upon completion of the penetrating stroke, preventing further relative movement. In either case, the depth of penetration of the needle into the patient's body is assured.

A feature of the present invention is that the cam surface may include upper and lower cam lockouts. The lower cam lockout fixes the needle in its extended position, wherein the needle may be connected to an infusion source to deliver drugs or other liquids to the bone marrow. The upper cam lockout fixes the needle in its retracted position, providing assurance that, prior to penetration or after retraction, the needle will not be available for spiking the user.

Another feature of the present invention is a spring between the base and upper frame for assisting counter rotation of the upper frame until the needle is fully retracted and locked into the upper cam lockout. Other features include a needle guide and suture hooks in the base and window ports in the upper frame.

Other features and advantages of the present invention should become apparent from the following description of the preferred embodiment, taken in conjunction with the accompanying drawings, which illustrate, by way of example, the principles of the invention.

DETAILED DESCRIPTION OF THE PREFERRED EMBODIMENTS

Figure 1:
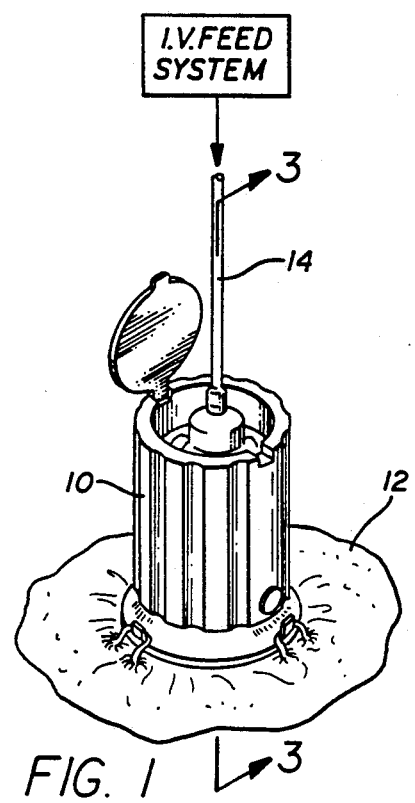
FIG. 1 is a perspective view of an intraosseous infusion device embodying the present invention sutured to a desired area of a patient's body.
Figure 4:
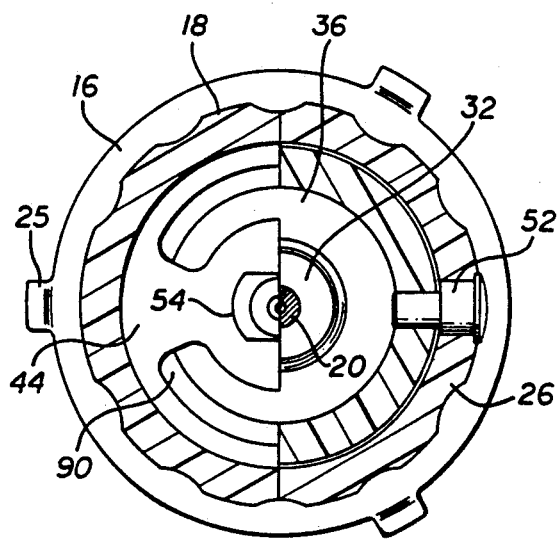
FIG. 4 is a sectional view of the intraosseous infusion device shown in FIG. 3 taken along the line 4—4.

An intraosseous infusion device 10 embodying the features of the present invention is shown in FIGS. 1-4. In FIG. 1, the device 10 is shown sutured to a patient's body 12 with an IV feed system 14 connected to it. The device 10 delivers a liquid (e.g., whole blood, lactated Ringers, hypertonic saline dextran, or a drug solution) from the IV feed system to the bone marrow of the patient's bone. The device is particularly useful in rapidly and reliably providing vascular access for infusion of the liquids into patients for whom there is a difficulty in utilizing the more common vascular infusion, due for example to low blood pressure brought on by severe circulatory shock or hemorrhaging or by small vessel size. Suitable bones include for example the manubrium (sternum), distal femur, proximal tibia, and iliac crest, which are all relatively large and located very close to the skin.

The intraosseous infusion device 10 includes a base 16, an upper frame 18, and an elongated needle 20. The base is generally tubular in shape and has a lower portion 22 that is flared outwardly. The lower portion includes a generally flat lower annular surface 24 for placement against the patient's body 12 adjacent the bone into which the liquid is to be infused. Suture hooks 25 may be formed on the outer periphery of the lower portion of the base. An upper portion 26 of the base has a cylindrical outer surface 28 defining a pair of oppositely disposed cam slots 30. The base further includes a needle guide 32 traversely disposed below the cam slots. The needle guide defines an opening 34 for closely receiving and guiding the elongated needle in a longitudinal direction. The needle guide also acts as a support for the needle to prevent it from buckling during penetration into the patient's body. The needle guide also has an annular recess 36 for receiving a spring 38.

The upper frame 18 has a tubular shape and includes an inner cylindrical wall 40, an outer cylindrical wall 42 and a traversely extending needle mount 44. The needle mount includes a downward projection 46 concentric with the inner cylindrical wall of the upper frame. An annular space 48 is formed between the projection and the inner cylindrical wall for receiving the upper portion 26 of the base and the spring 38. A pair of oppositely disposed radial openings 50 are formed in the upper frame. A cam follower 52 is press fit, or otherwise fixed, within the openings. The cam followers have pin portions 53 that protrude inwardly into the cam slots of the base. Each pin portion engages a cam surface 55 on the cam slot.

A central passageway 49 extends completely through the projection 46 and the needle mount 44 of the upper frame. The needle mount preferably includes a fitting 54 for connecting a conventional infusion device, such as an auto injection canister, a gravity feed bag, or a syringe, to the central passageway. The lower end of the projection defines a recess 56 for receiving the elongated needle 20.

The elongated needle has a lower end 60, an upper end 62 and a bore 64 extending therebetween. A serrated hub 66 is formed on the upper end of the elongated needle. The serrated hub is mounted in the recess 56 of the projection to prevent rotation of the needle relative to the upper frame. The serrated hub is also bored to provide a fluid channel between the passageway 49 of the projection and the bore of the needle.

The lower end 60 of the elongated needle has a slight taper along its length toward a conical, orifice free tip 68. The taper promotes a good seal between the needle and bone. The tip of the needle is free of an orifice because orifices located there would tend to clog during penetration of the bone. Ports 70 are located behind (or upwardly of) the conical tip 68 and communicate with the bore 64 which is fluidically connected to the IV feed system. The ports 70 are staggered around the circumference of the needle and connected to slits 72 extending longitudinally along the side of the needle. The ports are also recessed below the surface level of the needle. This configuration and placement of the ports and the slits allow discharge of the drug from the ports, even if the ports are partially blocked by tissue globules (not shown) in the bone marrow. The multiport needle also enables high viscosity fluids to be injected via an auto pump or a pump which produces high pressures, as is often required for intraosseous infusion.

The cam slots 30 in the base are configured to permit the upper frame and needle to move longitudinally, via the cam followers 52, between an upper retracted position, wherein the tip 68 of the needle is above the lower annular surface 24 of the base, and a lower extended position, wherein the tip of the needle extends a predetermined distance below the lower annular surface of the base. The cam slots also extend circumferentially around the base, causing the upper frame and needle to rotate when moved between the retracted and extended positions. The cam design enhances the driving forces of the needle, permitting it to more easily penetrate the bone. Preferably, the needle rotates approximately 45° as it moves between the retracted and extended positions.

In the preferred embodiment, each cam slot 30 further defines an upper cam lockout 76 and a lower cam lockout 78. The upper cam lockout maintains the needle in the retracted position, protecting the operator from being inadvertently stuck by the needle. The lower cam lockout maintains the needle in the extended position, which occurs at the completion of the penetrating stroke. Dimples (not shown) may be formed into the cam surfaces 55 of the cam slots adjacent each cam lockout. The cam followers then ride over the dimples, locking them in place. Alternatively, the cam slot may simply be configured to have an abrupt change in direction to form each lockout.

Figure 2:
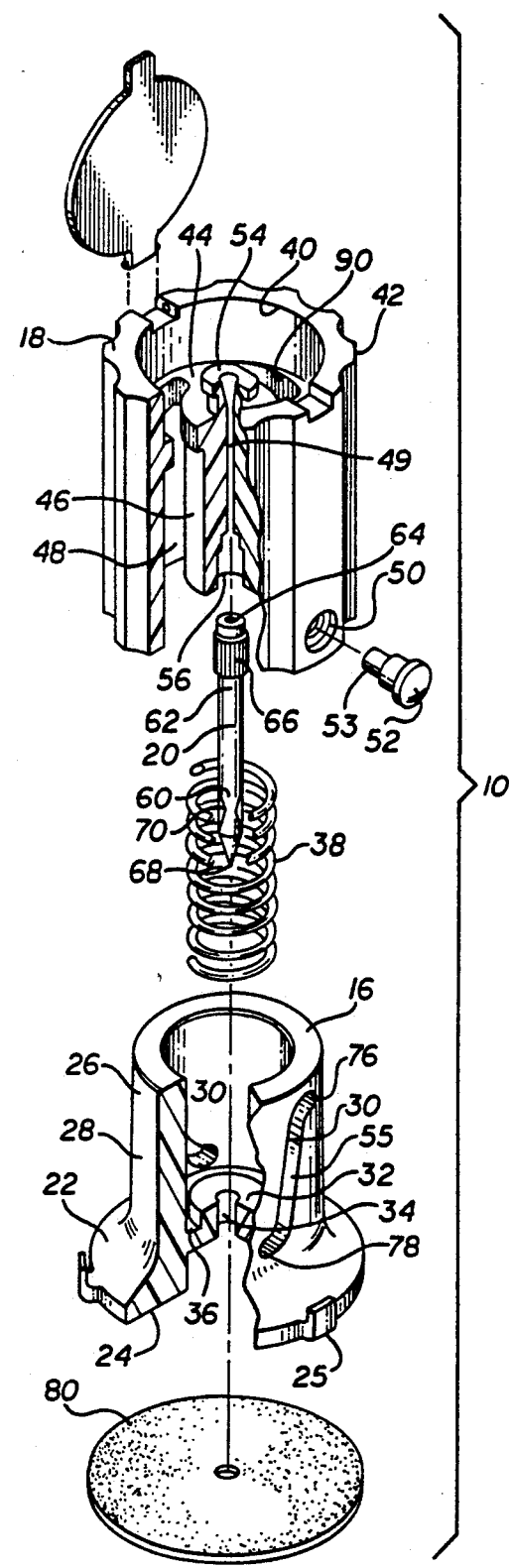
FIG. 2 is an exploded perspective view of the intraosseous infusion device shown in FIG. 1.
Figure 3:
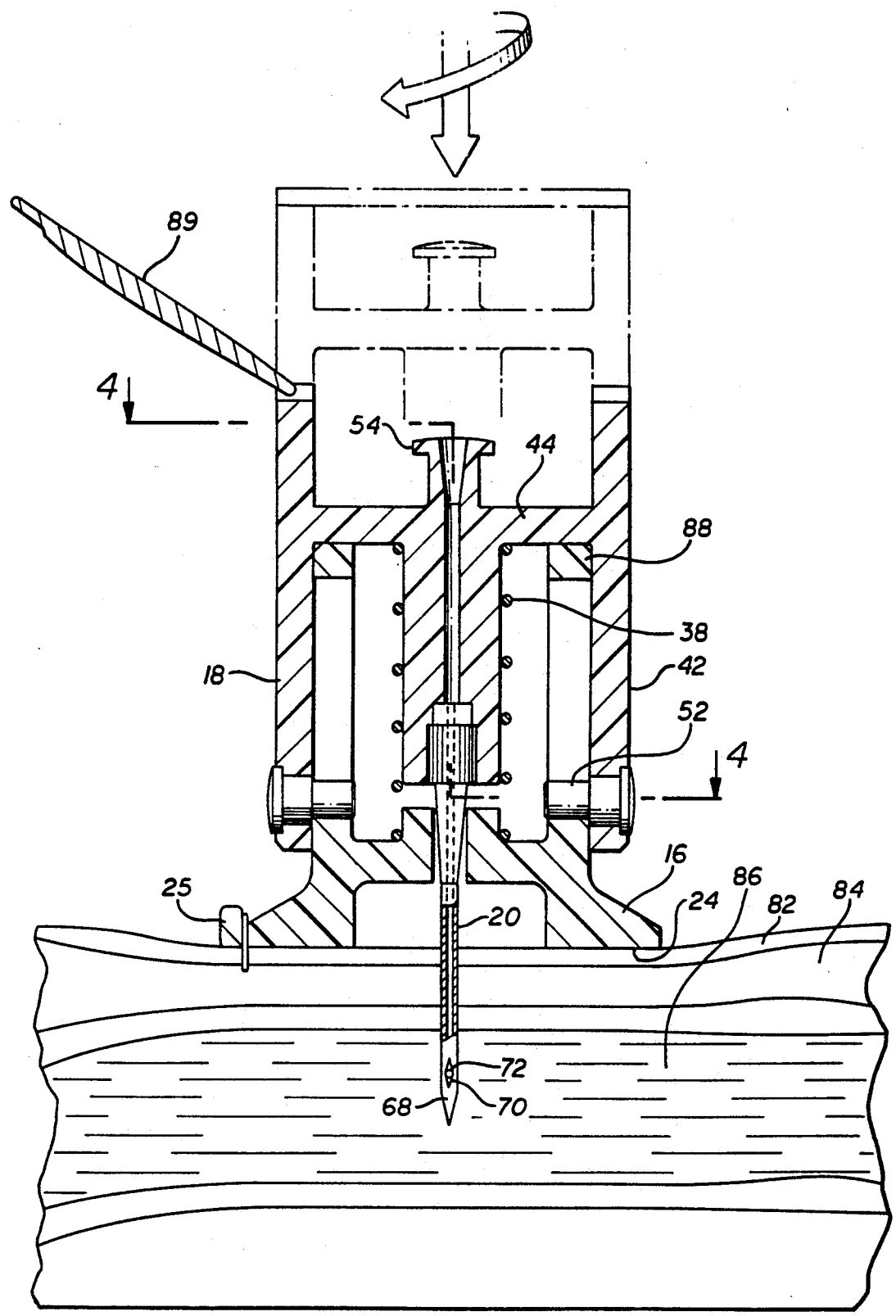
FIG. 3 is a sectional elevation view of the intraosseous infusion device shown in FIG. 1, taken along line 3—3, with the device shown in a retracted position (phantom lines) and an extended position (solid lines).

In use, the intraosseous infusion device of the present invention includes a medical adhesive pad 80 (FIG. 2). After removal of a protective cover (not shown) for the pad the device is placed on the desired portion of the patient's body. For example, in FIG. 3, the device is placed with the flat lower annular surface 24 of the base on the patient's skin 82 adjacent the patient's sternum 84. The base may be sutured into position for long term access via the suture hooks 25 incorporated into the base. The upper frame is then unlocked from the upper cam lockout 76, allowing the cam followers 52 to move along the cam surfaces 55 down the cam slots. The upper frame is then pushed down by an operator, wherein the needle 20 penetrates the patient's skin.

Due to the spiral shape of the cam slots, the needle rotates as it moves downward, assisting the needle in penetrating the patient's sternum. The length of the cam slot in the longitudinal direction is selected such that the needle ports 70 are located in the bone marrow 86 at the completion of the penetrating stroke. Alternatively, an upper surface 88 of the base may serve as a positive stop for the needle mount 44 of the upper frame, preventing further downward movement of the upper frame. The needle is locked in the extended position by rotating the cam followers into the lower cam lockout 78. The outer cylindrical wall 42 of the upper frame may be provided with finger grips to assist rotation.

A hinged lid 89 is then opened, which exposes the fitting 54, such as a LUHR type combined slip and bayonet fitting. Fluids may then be administered from an IV bag or needle. Window ports 90 may also be provided in the needle mount of the upper frame to permit visual inspection, e.g., to inspect for excessive bleeding or to confirm penetration of the needle.

Removal of the intraosseous infusion device is accomplished by holding the base in position and counter rotating the upper frame to remove the cam followers from the lower cam lockout. In the preferred embodiment, counter rotation is assisted by the spring 38 which urges the cam followers upward, removing the needle from the sternum bone until the needle is fully retracted and locked into the upper cam lock.

It will be appreciated that the base can have any number of shapes and sizes. Requirements for the base are that it (1) provide lateral support and alignment for the upper frame and stabilize the device on the patient's skin when installed, (2) serve as a support for the spring, and (3) provide a grip surface for the operator turning the upper frame relative to it. Similarly, the upper frame can have any number of shapes and sizes, the only significant requirement being that the operator be able to conveniently grasp it. A suitable surface texture or other irregularity on the upper frame's outer surface will facilitate such grasping.

The base and upper frame may be made from any suitable material having the requisite strength to withstand normal handling. The base may have at least limited pliability and its lower surface may be slightly concave shaped so as to securely engage the patient's skin. Preferably, the base is made from a clear plastic material to enhance viewing through the window ports 90.

It will be appreciated from the foregoing description that the present invention provides an intraosseous infusion device that is safe, effective, and easy to use. The device is self-threading and the penetrating stroke of the needle is preset to assure access to the sternum bone marrow, or other bone marrow, allowing the needle port to infuse drugs, plasma, etc. into the vascular system.

It will, of course, be understood that modifications to the presently preferred embodiment will be apparent to those skilled in the art. Consequently, the scope of the present invention should not be limited by the particular embodiments discussed above, but should be defined only by the claims set forth below and equivalents thereof.

I claim:

1. An intraosseous infusion device for delivering a liquid to the bone marrow of a patient's bone, the device comprising:
   a base having a lower surface configured for placement against the skin of the patient, adjacent to the patient's bone, wherein an opening extends through the base, emerging in its lower surface;
   an upper frame mounted to the base;
   an elongated needle having a lower end, an upper end and a bore extending therebetween, the lower end of the needle having a tip suitable for puncturing the patient's skin and a port communicating with the bore of the needle, the upper end of the needle fixedly mounted to the upper frame; and
   a fitting for receiving liquid to be delivered to the patient's bone marrow and for supplying the liquid to the bore at the upper end of the needle;
   wherein one of the base and the upper frame has a cam surface and the other of the base and the upper frame has a cam follower that engages the cam surface, the cam surface and the cam follower disposed relative to each other such that the upper frame is movable in a longitudinal direction between a retracted position wherein the needle tip does not extend below the lower surface of the base and an extended position wherein the needle tip does extend below the lower surface of the base; and
   wherein the cam surface is configured to cause the upper frame to rotate relative to the base as the upper frame moves longitudinally between the retracted and extended positions.

2. The intraosseous infusion device of claim wherein the upper frame defines a passageway having an upper end and a lower end, the upper end of the passageway fluidically connected to the fitting and the lower end of the passageway fluidically connected to the bore of the needle.

3. The intraosseous infusion device of claim wherein the needle rotates approximately 45 degrees relative to the base as the upper frame moves between the retracted and extended positions.

4. The intraosseous infusion device of claim wherein the cam surface includes an upper cam lockout for maintaining the upper frame in the retracted position.

5. The intraosseous infusion device of claim wherein the cam surface includes a lower cam lockout for maintaining the upper frame in the extended position.

6. The intraosseous infusion device of claim wherein the cam surface includes an upper cam lockout for maintaining the upper frame in the retracted position and a lower cam lockout for maintaining the upper frame in the extended position.

7. An intraosseous infusion device for delivering a liquid to the bone marrow of a patient's bone, the device comprising;
   an elongated needle having a lower end, an upper end and a bore extending therebetween, the lower end of the needle having a tip suitable for puncturing the patient's skin and a port communicating with the bore of the needle;
   a substantially tubular base having an upper portion, a lower portion and a traversely extending needle guide between the upper and lower portions, the needle guide having a centrally located opening for closely receiving the elongated needle, the lower portion having a lower surface for placement against the skin of the patient;

a tubular upper frame mounted to the base, the upper frame having a traversely extending needle mount for holding the upper end of the needle, the needle mount defining a passageway for receiving liquid to be delivered to the patient's bone marrow and for supplying the liquid to the bore of the needle;

wherein the upper end of the tubular base has a cam surface and the tubular upper frame has a cam follower that engages the cam surface, the cam surface and the cam follower disposed relative to each other such that the tubular upper frame is movable in a longitudinal direction between a retracted position wherein the needle tip does not extend below the lower surface of the base and an extended position wherein the needle tip does extend below the lower surface of the base; and wherein the cam surface is configured to cause the tubular upper frame to rotate relative to the base as the tubular upper frame moves longitudinally between the retracted and extended positions.

8. The intraosseous infusion device of claim 7, wherein the upper portion of the base has an upper surface that is in contact with the needle mount when the tubular upper frame is in a fully extended position.

9. The intraosseous infusion device of claim 7, wherein a spring is disposed between the needle guide and the needle mount for urging the tubular upper frame to its retracted position.

10. The intraosseous infusion device of claim 7, wherein the needle mount includes a window port.

11. The intraosseous infusion device of claim 7, wherein the lower portion of the tubular base includes a plurality of suture hooks.

* * * * *

UNITED STATES PATENT AND TRADEMARK OFFICE
CERTIFICATE OF CORRECTION

PATENT NO. : 5,312,364
DATED : May 17, 1994
INVENTOR(S) : Michael W. Jacobs

It is certified that error appears in the above-identified patent and that said Letters Patent is hereby corrected as shown below:

Column 6, line 33, after "claim" insert --1--.

Column 6, line 39, after "claim" insert --1--.

Column 6, line 43, after "claim" insert --1--.

Column 6, line 46, after "claim" insert --1--.

Column 6, line 49, after "claim" insert --1--.

Signed and Sealed this

Thirtieth Day of August, 1994

Attest:

BRUCE LEHMAN

*Attesting Officer*  Commissioner of Patents and Trademarks